United States Patent [19]

Kisner

[11] 4,400,255
[45] Aug. 23, 1983

[54] CONTROL OF ELECTRON BOMBARDMENT OF THE EXHAUST OXYGEN SENSOR DURING ELECTRODE SPUTTERING

[75] Inventor: Howard D. Kisner, Wichita Falls, Tex.

[73] Assignee: General Motors Corporation, Detroit, Mich.

[21] Appl. No.: 278,049

[22] Filed: Jun. 29, 1981

[51] Int. Cl.³ .............................................. C23C 15/00
[52] U.S. Cl. ........................ 204/192 SP; 204/192 S; 204/192 C; 204/427
[58] Field of Search ...................... 204/192 SP, 195 S

[56] References Cited

U.S. PATENT DOCUMENTS

| | | | |
|---|---|---|---|
| 3,844,920 | 10/1974 | Burgett et al. | 204/195 S |
| 4,083,764 | 4/1978 | van de Leest et al. | 204/192 SP |
| 4,107,018 | 8/1978 | Bode | 204/192 SD |
| 4,136,000 | 1/1979 | Davis et al. | 204/195 S |
| 4,169,777 | 10/1979 | Young et al. | 204/195 S |
| 4,186,071 | 1/1980 | Romine et al. | 204/195 S |
| 4,244,798 | 1/1981 | Gold et al. | 204/192 SP |
| 4,253,394 | 3/1981 | Berg et al. | 204/195 S |
| 4,253,931 | 3/1981 | Gold et al. | 204/192 SP |
| 4,264,647 | 4/1981 | Trevorrow | 204/195 S |
| 4,328,080 | 5/1982 | Harris | 204/192 EC |

*Primary Examiner*—Arthur P. Demers
*Attorney, Agent, or Firm*—Robert J. Wallace

[57] ABSTRACT

A method of sputtering a platinum exhaust gas electrode onto a vitrified zirconia thimble for an electrochemical-type exhaust gas oxygen sensor. High yields of sensors having fast response times as formed are consistently produced. The exhaust gas outer electrode is sputtered onto the thimble after first forming an inner electrode, using a rate that significantly heats the thimble. The first electrode is maintained electrically isolated from the exhaust electrode during sputtering, and is maintained at a different electrical potential.

4 Claims, 1 Drawing Figure

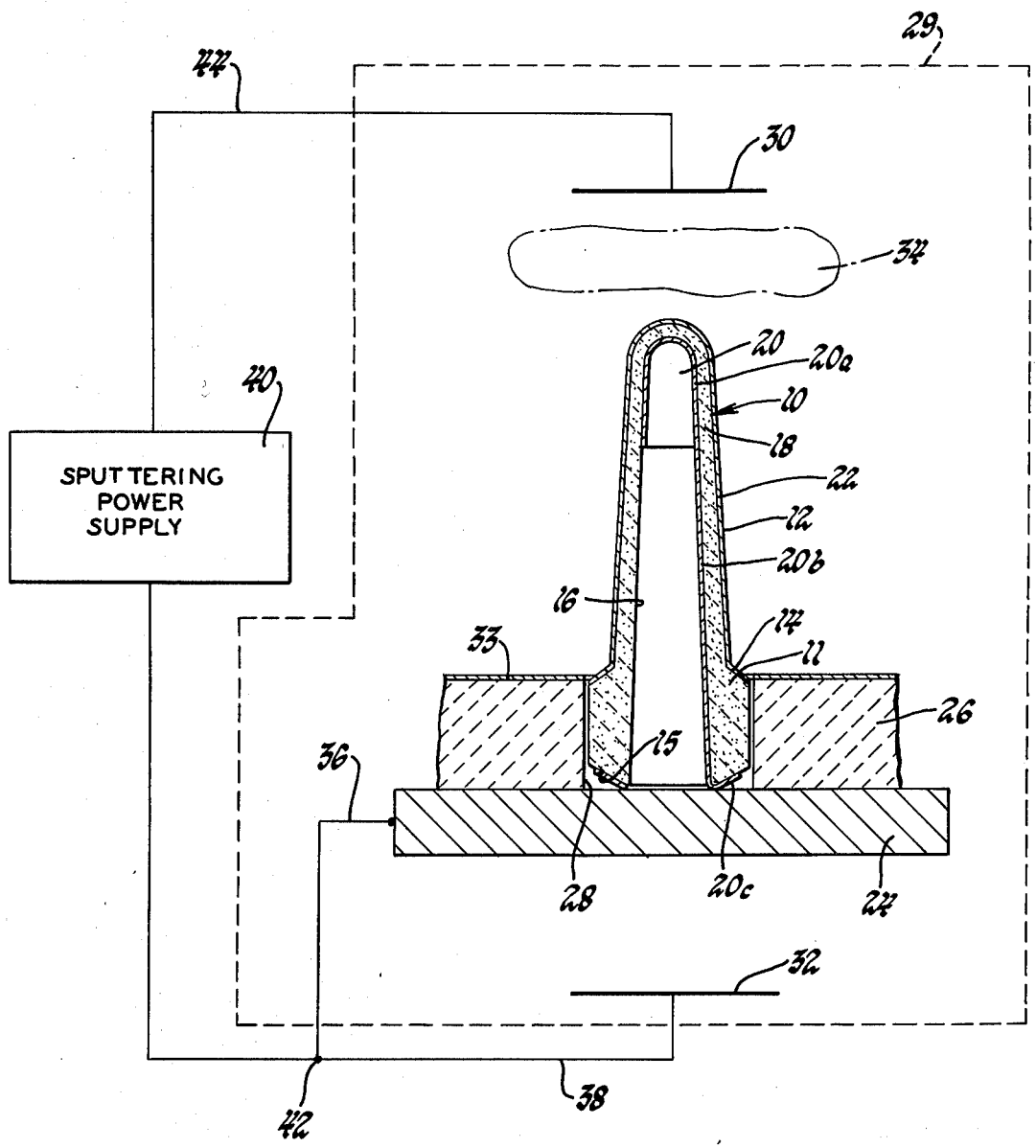

CONTROL OF ELECTRON BOMBARDMENT OF THE EXHAUST OXYGEN SENSOR DURING ELECTRODE SPUTTERING

FIELD OF THE INVENTION

This invention relates to solid electrolyte, electrochemical-type exhaust gas oxygen sensors. It more particularly relates to a sputtering process for depositing a platinum exhaust electrode onto vitrified zirconia thimbles for such sensors.

BACKGROUND OF THE INVENTION

A typical automotive-type solid electrolyte exhaust gas oxygen sensor is disclosed in U.S. Pat. No. 3,844,820 Burgett et al. It has a zirconia sensing element shaped as a tapered thimble. One end is opened and has a thick circumferential flange. The other end is disclosed and forms the most active part of the element. The interior and exterior of the thimble has separate porous inner electrode coatings of platinum or the like.

The inner electrode is exposed to a known source of oxygen, such as air or a mixed metal oxide, for establishing a reference potential. This electrode is generally formed by painting a coating of platinum ink into the zirconia thimble, drying the coating, then firing the coated thimble at an elevated temperature. The composition and dimensions for such a thimble, and an improved technique for applying the reference electrode, is disclosed in U.S. Pat. No. 4,264,647 entitled "Reference Electrode Printing Process and Mask for Exhaust Gas Oxygen Sensor", which was filed on Oct. 1, 1979 in the name of John Trevorrow.

The outer electrode is usually formed by thin film techniques, such as evaporation or sputtering. Improved sputtering techniques for applying the outer, i.e. exhaust, electrode are disclosed in U.S. Pat. No. 4,253,931 Gold et al; and U.S. Ser. No. 189,732 Gold et al.

U.S. Pat. No. 4,253,931 describes an improved sputtering process which involves the use of nitrogen and/or oxygen along with argon as a pressure of about 10-20 millitorr to provide higher yields of fast responding sensors as formed. It also discloses a wide target thimble spacing of about 3.8 cm along with a high sputtering of 13-22 watts/cm$^2$ of target area. The foregoing improved sputtering techniques all help produce sensors having fast average sensor response times without artificial ageing. However, it must be recognized that the zirconia thimbles were coated on a batch basis, and that not all thimbles in a given sputtering batch will exhibit the same fast response time when assembled into finished sensors. U.S. Pat. No. 4,253,934 Berg et al describes salvaging the thimbles producing slower response times by nitrogen ageing them. This involves treating them in substantially oxygen-free nitrogen at an elevated temperature. However, there is no practical way to discern a fast responding thimble from a low responding thimble, before assembly into a finished sensor. Thus, an effective way to insure highest yield of fast responding sensors, is to nitrogen age all of the thimbles before assembly into sensors. The increase in yield has been sufficient to offset the costs of such a treatment.

I have now found a further improvement in the aforementioned sputtering techniques, which can provide a still further improvement in yield of fast responding sensors. The yield increase appears to be so significant that it may even obviate the significant benefits attributable to the nitrogen ageing treatment of the aforementioned U.S. Pat. No. 4,253,934 Berg et al. Tests have shown a yield increase that makes the additional nitrogen ageing treatment of questionable economic value. In the very least, my improved process should provide an improvement in yield even after the nitrogen artificial ageing of the Berg et al U.S. Pat. No. 4,253,934. In other words, one can consider my invention provides a faster average sensor response time.

OBJECTS AND SUMMARY OF THE INVENTION

An object of this invention is to provide an improved sputtering process for depositing a platinum exhaust electrode onto a zirconia solid electrolyte body for an electrochemical-type exhaust gas oxygen sensor.

The invention comprehends sputtering platinum onto the exterior surface of a vitrified zirconia thimble while the inner surface of the thimble is maintained at an electrical potential similar to that of the sputtering anode and a low resistance connection between the inner and outer thimble surface is precluded. Sputtering is conducted at a high enough rate to make the thimble significantly electrically conductive. It is terminated after an appropriate period of electron bombardment of the outer surface.

BRIEF DESCRIPTION OF THE DRAWING

Other objects, features and advantages of the invention become more apparent from the following description of preferred examples thereof and from the drawing in which:

The FIGURE diagrammatically shows a sputtering apparatus for practicing this invention and includes an enlarged fragmentary view of a sputtering substrate carrier and mask.

DESCRIPTION OF THE PREFERRED EMBODIMENTS

Tapered vitrified zirconia thimbles for an exhaust gas oxygen sensor contemplated by this invention are shown and described in the aforementioned patents and applications. One example that is currently being manufactured is a hollow thimble 10 about 3–5 cm long, made of zirconia partially or fully stabilized in its cubic form by the inclusion of about 4–8 mole percent yttria. Each thimble has a taper on its outer surface of about 3 degrees—38 minutes. In one particular example, it has an axial length of about 3.66 cm. Its open end has a thick radial flange 11, that forms a circumferential shoulder 14 on the thimble outer surface 12. The shoulder is about 0.25 cm wide. The flange 11 has an axial length of about 0.6 cm between shoulder 14 and a chamfer 15 on the thimble bottom end. The outer diameter of flange 11 is about 1.3 cm. The outer surface 12 of thimble 10 has a diameter of about 0.82 cm immediately adjacent shoulder 14 in a direction away from flange 11. The narrow end of the thimble 10 is closed and rounded, having an external spherical radius of curvature of about 0.2 cm. Its external diameter adjacent the rounded end is about 0.3 cm. The interior surface 16 of hollow thimble 10 is also tapered but slightly less than the taper on outer surface 12, so as to provide a thinner wall 18 adjacent the closed end of the thimble than adjacent the thimble open end at shoulder 14.

In this invention, an inner reference electrode 20 is formed on the inner surface 16 of hollow thimble 10 before an exhaust electrode 22 is sputtered onto the outer surface 12. I prefer to form the inner electrode 20 as described in the aforementioned U.S. Pat. No. 4,264,647 Trevorrow. In summary, the platinum ink is uniformly coated onto inner surface 16 using a distinctive coating process and apparatus. The ink is then dried and heated in air to fire it to the inner surface 16. Inner electrode 20 has a continuous circumferential upper portion 20a on the entire upper end of the thimble inner surface 16. An axial stripe 20b extends down from the upper circumferential electrode portion 20a to the open, i.e. bottom, end of the thimble where it intersects a second continuous circumferential portion 20c of the electrode coating 20, on the butt end of the thimble 10. Coating 20c is thus in direct contact with the stainless steel pallet 24 which supports the thimble 10. Inner electrode coating portion 20c thus provides a low resistance contact between pallet 24 and the upper electrode portion 20a on the inner surface 16 of thimble 10. The thimble is then cleaned to receive a thin film exhaust electrode on outer surface 12 in accordance with this invention.

It should be understood that this invention should be used to simultaneously sputter outer electrodes on hundreds of zirconia thimbles at the same time. However, to better focus on the new and different facets of this invention only one such thimble is shown in the drawing, along with only a fragment of an associated masking and support assembly. Thimble 10 is shown supported on a planar steel plate 24, which serves as a pallet. Pallet 24 also supports a masking plate 26. Masking plate 26 has an aperture 28 within which the flange 11 of thimble 10 is nested. Machining plate 26 prevents a low resistance electrical connection from occurring between electrodes 20 and 22 during sputtering.

The outer surface 12 of thimble 10 can be prepared to receive the thin film sputtered platinum electrode 22 by cleaning in any normal and accepted procedure. One cleaning procedure that can be used includes ultrasonically degreasing the zirconia thimble 10 with freon, and then heating it to about 600° C. in air for about one hour. Masking plate 26 is placed on the pallet 24. Masking plate 26 has a uniform array of 418 holes, only one of which is shown and is designated by reference numeral 28. The holes are arranged in orthogonally oriented columns and rows. The holes all have a diameter of about 13.42 mm. Each column has 19 holes, on centers spaced 16.33 mm apart. 22 columns are used. Adjacent columns are staggered, with adjacent columns having their center lines spaced 13.28 mm apart.

A clean thimble is loaded in each aperture 28 of the ceramic plate 26, so that the thimble axis is oriented vertically and the thimble open end is down. Pallet 24 thus supports a plurality of thimbles in a uniform way, even though only one is shown. The pallet 24 is then placed directly into a vacuum chamber for sputtering. The vacuum chamber is indicated by a dashed line in the drawing and is designated by a reference numeral 29. At this point, the thimbles 10 are ready for sputtering. However, if they are not to receive their outer, i.e. sputtered, electrodes within 72 hours after the last-mentioned heating, they should be heated again to 600° C. for about one hour, and then again at about 150° C. for about 45 minutes to two hours immediately before sputtering.

I have sputtered the outer electrode 22 with a model MRC 902 DC magnetron sputtering apparatus obtained from Materials Research Corporation, Orangeburg, N.Y. It has an elongated fairly shallow vacuum chamber with provision for two fixed targets disposed over a single fixed anode that is much larger than the targets. For completeness of disclosure, details of this apparatus are hereinafter described.

The targets are essentially two rectangular mutually spaced parallel metal strips oriented transverse to a rectangular stainless anode. In the drawing, one target is shown, disposed over thimble 10. It is indicated by reference numeral 30. A sputtering anode 32 is disposed below pallet 24. Anode 32 is about 35 cm wide, 50 cm long and 2-3 cm thick. It is spaced about 1 cm above the bottom wall of main chamber 29. Water cooling of the anode is not necessary but may be beneficial for reduced cycle time.

I choose to ordinarily use only one of the targets in the MRC 902. Its targets and anode are in a main chamber 29 adjacnet an antechamber (not shown) having an elevator mechanism (not shown) that can stack two pallets. I refer to the antechamber as a load-lock. A movable sealing means (not shown) separates the antechamber from the main chamber 29. A special carrier (also not shown) is provided for shuttling the pallet 24 of thimbles from the antechamber into the main chamber 29 for sputtering and then back again. In sputtering a discharge 34 at the desired power setting is first established between the target 30 and the anode 32. Then the carrier moves the pallet 24 between them. It continues to move in the same direction until it is out from under the target 30, whereupon the discharge is discontinued. Carrier speed is adjusted to obtain the desired coating weight, which is indicative of a given electrode average thickness. When using the aforementioned apparatus, the main chamber 29 is substantially always maintained under sputtering atmosphere conditions or high vacuum except for apparatus servicing.

While one batch of thimbles is being coated in the main chamber 29, another is being removed from the antechamber, a new batch placed in the antechamber, and the antechamber returned to low pressure. To load the apparatus, a pallet of thimbles is placed in the antechamber while it is sealed from the main chamber and is at ambient pressure. The antechamber is then sealed to the ambient and evacuated to about 100 millitorr. After electrodes have been sputtered onto a first batch of thimbles in the main chamber, sputtering is discontinued and the seal between it and the antechamber is opened. The first pallet of thimbles is shuttled to one level of the antechamber elevator, which picks it off the pallet carrier. The elevator is moved to a new level and the just loaded pallet is placed on the pallet carrier. The pallet carrier then moves back into the main chamber 29 far enough to close the antechamber-main chamber seal but not so far as to be under the target 30. At this point the main chamber 29 is sealed from the antechamber, the antechamber backfilled with dry nitrogen to atmospheric pressure, whereupon it can be opened to the ambient for revmoval of the electroded first thimble pallet and reloaded.

The main chamber is pumped down to below $5 \times 10^{-6}$ torr. A flow of about 50-70% by volume nitrogen and 30-50% by volume argon, preferably 60% nitrogen and 40% argon by volume, is then introduced into the main chamber at a rate of about 75-100 cc per minute, while pumping continues. Pumping is then throttled at a sufficient rate to dynamically maintain a pressure in the main chamber of about 10–20 millitorr. Once pressure is the main chamber is stabilized, a glow discharge 34 can be established between the target 30 and the anode 32. Pressure is maintained at this level in this way during sputtering, as is usual. In the apparatus and under the conditions described herein, I can simultaneously electrode batches of 418 thimbles. When the thimbles are placed on the pallet 24, they are all oriented vertically and thus have parallel vertical axes. Their closed ends are upwardly disposed, so as to be adjacent the glow discharge 34 during sputtering. Their open lower ends directly contact steel pallet 24. The pallet currently used is about 31 cm long, 31 cm wide, and about 1.8 cm thick. The masking plate 26 is 0.82 cm thick. The axial length of flange 11 is about 0.75 cm, between the shoulder 14 and the thimble bottom end. Hence, masking plate 26 is slightly thicker than flange 11 is long. The difference is sufficient to provide a significant step between the thimble shoulder 14 and the upper surface of masking plate 26. This step can be of any dimension which, in combination with the thimble-hole spacing, will produce a discontinuity in the sputtered platinum coating between electrode 22 and the portion 33 on the upper surface of masking plate 26. In such event, the masking plate 26 need not be made of ceramic, as shown in the drawing. This discontinuity between electrode 22 and coating 33 will produce electrical isolation between inner electrode 20 and outer electrode 22 even if ceramic plate 26 is made of aluminum. However, to emphasize the electrical isolation that is needed in this invention between electrode 22 and the pallet 24 I have chosen to show plate 26 to be of ceramic. However, if made of ceramic, a discontinuity must still be insured elsewhere on the surface or edge of the ceramic plate, if not provided by the aforementioned step. It can be provided, for example, by a peripheral groove on the edge of the ceramic plate.

It should also be mentioned that whether plate 26 is of ceramic or of aluminum it must be periodically cleaned to prevent the buildup of coating 33 to such an extent that it can bridge across the edge of hole 28 onto the shoulder 14, and make electrical contact with electrode 22. One can prevent this gap from being bridged by maintaining the upper surface of plate 26 sufficiently above shoulder 14 and/or maintaining hole 28 somewhat larger than the outer diameter of flange 11 on the thimble, and periodically removing platinum coating portion 33. Further, I presume that still other means can be used to maintain electrical isolation between the inner and outer electrodes 20 and 22 during sputtering. Incidentally, I prefer to include a plurality of grooves in the upper surface of the plate 24 that are narrower than the thimble inner diameter and registered with rows of holes in the masking plate 26. The grooves may facilitate evacuating thimble interiors.

The pallet 24 is supported by five stainless steel cylinders (not shown) each of which is about 1.3 cm long and about 0.6 cm in diameter. These cylinders are in turn supported by the stainless steel pallet carrier, which has a U-shaped configuration when viewed from above. The stainless steel cylinders are appropriately spaced along the "U" to support pallet 24. The pallet carrier has stainless steel axles and wheels, that ride on the bottom wall of the stainless steel main chamber 29. Pallet 24 is in low resistance electrical communication with the wall of chamber 29 through the pallet carrier, its axles and wheels. Since the wall of chamber 29 is electrically at the same potential as anode 32, the pallet 24 is thus maintained at about the same electrical potential as anode 32. This relationship is schematically indicated in the drawing by showing an electrical conductor 36 extending from pallet 24 to an electrical lead 38, where it is connected at 42. Lead 38 extends from a sputtering power supply 40 to anode 32. Target 30 is schematically shown connected to the sputtering power supply 40 through lead 44. Target lead 44 must insulatingly pass through the wall of main chamber 29. However, conductor 36 and anode lead 38 need not be so insulated. It was previously mentioned that the inner surface 16 of thimble 10 is in low electrical resistance with pallet 24 through the inner electrode portions 20a, 20b and 20c. Hence, the inner surface 16 of thimble 10 is maintained at about the same electrical potential as the anode 32.

In the past, the cylinders used to support the pallet on the pallet carrier were generally made of ceramic and served to electrically isolate the thimbles from the anode. For this reason they have heretofore been referred to as standoffs. The pallet carrier supports the pallet 24 about 0.5–1.5 cm above the sputtering anode. However, I do not know if any separation at all is needed, particularly since in this invention pallet 24 is at about the same electrical potential as the anode 32. Incidentally, other means than those hereinabove described can be employed for maintaining both the pallet and the anode at substantially the same potential, if desired.

After the antechamber seal is opened, the pallet is transferred onto the pallet carrier. The pallet carrier is shuttled to its initial position adjacent but not under the planar platinum target 30. When so positioned the thimble closed ends are spaced about 3.8 cm below a line extended from the surface of the target 30.

Target 30 is a rectangular platinum sheet about 12 cm × 38 cm × 0.6 cm bonded to a supporting copper backing plate. The nature of the platinum target is no more critical to this invention that it is to any other sputtering of platinum. The target can be obtained from any commercial source, and preferably provides a high purity platinum surface. While I presently do not prefer it I recognize that in some instances it may prove to be desirable to include minor amounts of other metals in the platinum target along with the pure platinum, as for example up to about 5% by weight palladium and/or rhodium. The target is assembled with a cathode that includes water cooling means and a magnet array. The magnets are arranged to produce as uniform an erosion as possible on the platinum surface of the target 30 as well as a uniform thermal and electron flux from the plasma 34 onto the array of thimbles 10 on the pallet 24.

As with the aforementioned U.S. Pat. No. 4,253,931 Gold et al, sputtering is preferably accomplished with a sizeable precentage of nitrogen and/or oxygen present. Nitrogen is preferred because of handling problems associated with oxygen. I prefer to use a mixture of 60% nitrogen and 40% argon, by volume, to attain best results. In the past a 75/25 mixture was preferred when the thimbles were allowed to float electrically.

I still prefer the wide thimble to target minimum spacing of at least about 3.0 cm and generally less than about 4.5–5.0 cm. A DC voltage of about 500–800 volts is applied between the target 30 and the anode before the thimbles are shuttled between them. The sputtering power supply is adjusted to provide a DC power of about 4–8 kolowatts, which is the same DC power used in the aforementioned U.S. Pat. No. 4,253,931 Gold et al, i.e. 13–22 watts/cm$^2$ of target area.

As previously mentioned, the pallet carrying thimble 10 is moved through the plasma 34 to produce the sputtered coating 22. Movement is not started until plasma 34 has stabilized. Then, the movement starts and the upper tips of the thimbles 10 traverse through the plasma at a uniform rate of 4 to 5 cm per minute. No supplemental means are used to heat the pallet, pallet carrier or anode during sputtering, or for that matter to cool them. The pallet movement rate is adjusted to obtain a platinum electrode 22 having an average weight of about 10 milligrams on each of the 418 thimbles being simultaneously coated, in just one pass under target 30. Less than 9 mg of electrode, under the conditions of this example, does not provide a sufficient average improvement in electrode performance. Under the source sputtering conditions, more than 11 mg can produce negative voltages when the sensor is sensing lean air/fuel mixtures.

In general, a platinum electrode 22 having a weight of about 10 milligrams will have a thickness of about 1.0–1.5 micrometers thick on the upper ends of the zirconia thimbles 10. The upper ends of the thimbles will get the greatest thickness of platinum. Side walls on the element will get a correspondingly lesser platinum deposit down to the shoulder 14, where it increases in thickness. About 10 milligrams of platinum will provide an electrode 22 having a thickness of 0.65–1.0 mm thick at a point about 0.5 cm back from the thimble closed end, along with a coating thickness of about 0.3–0.55 micrometer thick about 2 cm back from the thimble closed end.

After all 418 thimbles on pallet 24 have passed through the glow discharge 34, the sputtering power supply 40 is turned off, and the glow discharge discontinued. The pallet 24 can then be shuttled back into the antechamber for unloading as previously described.

After being unloaded from the sputtering chamber, the thimbles can be heated in air for one hour at about 800° C. to increase electrode adhesion. This increase in adhesion can be obtained by heating over a rather wide temperature range, extending from about 600° to about 1200° C. However, it should be recognized that heat treatments above about 800° C. tend to sinter electrode coating 22, which can open large pores in it as well as form isolated platinum islands. This is obviously objectionable. A porous coating of magnesium-aluminate spinel can then be flame sprayed onto the platinum electrode 22, leaving a portion of the electrode uncovered at and near shoulder 14 for making of a low resistance electrode connection to electrode 22. It is recognized that the flame spraying of a ceramic overcoat onto the thin electrode may drastically alter the physical appearance of the film. On the other hand, it does not appear to deleteriously affect controllability of switching response times produced by this invention. Electrical characteristics still remain that are attributable to the nature of the electrode as it was initially deposited.

Each coated thimble can then be assembled into a sensor such as illustrated in the aforementioned U.S. Pat. No. 3,844,920. The resultant sensor assembly consistently exhibits fast switching response times, that are similar for both rich-to-lean and lean-to-rich changes. It also exhibits a controllability closer to stoichiometry. For example, a rich-to-lean time response of less than 100 milliseconds can be consistently obtained for over 90% of the sensors made from such elements, even if the sensors have not been previously artifically aged in nitrogen pursuant with the aforementioned U.S. Pat. No. 4,253,934 Berg et al.

It appears that optimum sputtering conditions will provide an electrode 22 that is within the thickness range previously mentioned and which has a weight of approximately 10 milligrams for the size of thimble which has been described herein. I have obtained data that indicates this thickness corresponds to the total optimum energy that should be applied to the thimble during sputtering. I believe that in this invention the thimbles react in a unique way to the bombardment of electrons from plasma 34. When the inner electrode 16 is maintained at substantially the same electrical potential as the anode 32, electrons from the plasma 34 can only be attracted to the outer surface 12 of thimble 10, i.e. electrode 22, as it is being deposited. They do not initially become attracted to inner electrode 20, and then at some unknown and uncontrolled point in the sputtering process become attracted to electrode 22. The bombarding electrons provide a constant lower electrical potential on thimble outer electrode 22 than on thimble inner electrode 20. This potential difference is maintained throughout the sputtering duration. It insures that the inner surface 16 underneath electrode 20 remains completely oxidized after sputtering but concurrently causes outer surface 12 beneath electrode 22 to be somewhat reduced. I believe that this action insures that a greater percentage of the thimbles in the batch will provide acceptably fast response times as formed.

Cross sections of the fastest responding thimbles show a decided darkening of zirconia at its interface with electrode 22. This darkening is attributable to the presence of free zirconium at and just below surface 12, i.e. under electrode 22. Optimum sputtering conditions appear to provide a darkening at this interface without the darkening proceeding to any appreciable depth. The particular thickness of this darkening does not appear to be particularly significant. On the other hand, it must not extend through the entire thickness of wall 18. If it does, the resultant sensor is likely to have a negative lean voltage, instead of the desired small positive voltage. The negative lean voltage makes the sensor incompatible with established control electronics and is therefore not useful. Information on the effect this darkening has on durability is not complete.

With the foregoing in mind it is apparent that the rate of deposition, i.e. sputtering power, is important to this invention. It must be appropriately balanced with the amount of electrode which is being deposited to produce the optimum improvement in sensor response time. In other words, the rate of deposition is adjusted to provide just the correct amount of total energy in the form of electron bombardment and heating of the thimble 10 to provide just the desired degree of conduction. I believe that the increasing electron conduction in the zirconia is even more important than increasing ionic conduction, to achieve the desired darkening effect under electrode 22.

It is obvious that sputtering conditions will have to be adjusted depending on the size of the thimbles, the quantity of thimbles being treated, the electrode weight which is desired, thimble wall thickness, the sputtering power, target efficiency, etc. All of these factors should be considered in obtaining the optimum sputtering conditions.

The benefits of this invention should be obtainable whether or not the electroded thimble is heated in air to increase electrode adhesion, given a porous overcoat, and/or heated in nitrogen according to the aforementioned U.S. Pat. No. 4,253,934 Berg et al. Still further, other porous overcoats than hereinbefore described can be used, as for example the gamma alumina coatings disclosed in U.S. Pat. No. 4,116,883 Rhodes. Also, it may be desirable to use a platinum cermet stripe on the outer surface of the zirconia thimble under the sputtered electrode 22, or at least where the porous overcoat does not cover it, to improve durability. If so, the cermet stripe can be previously applied, and fired at the same time as the inner electrode 20.

Further, it should be expected that the results of this invention should be obtainable regardless as to the nature of the reference electrode or its method of application. Analogously, these results should be obtainable on partially or fully stabilized zirconia having any other stabilizing agents than hereinbefore described. Further, the principle of this invention should be applicable to RF sputtering and DC sputtering as well as DC magnetron sputtering. Still further, the sputtering conditions of this invention should be useful in a single batch-type apparatus having no antechamber or in a continuous in-line processing apparatus that would include one or more controlled atmosphere chambers before and after the sputtering chamber. As previously mentioned, this invention permits higher yields of fast electrodes to be obtained as formed. Nonetheless, there will still be a few marginally acting electrodes. It appears that the artificial, i.e. nitrogen, aging treatment of the aforementioned U.S. Pat. No. 4,253,934 Berg et al can improve the response time of these marginal electrodes. However, it is questionable if the yield increase, over the yields of my invention, is sufficient to justify the expense of such a treatment.

The embodiments of the invention in which an exclusive property or privilege is claimed are defined as follows:

1. In a method of sputtering an exhaust electrode onto a given surface of a zirconia solid electrolyte exhaust gas oxygen sensor body, opposite from a surface on said body having a previously formed reference electrode, the improvement of:
   providing a low resistance electrical path between the reference electrode and a sputtering anode;
   sputtering an exhaust electrode onto said body while it is electrically conductive at a pressure of about 10-20 millitorr, a target-body minimum spacing of at least about 3.0 cm, and at a sputtering power of about 13-22 watts/cm$^2$ of target area used;
   heating said sensor body to make it significantly electrically conductive;
   maintaining the exhaust electrode electrically isolated from said reference electrode during said sputtering, so as to maintain a voltage difference between said surfaces during sputtering that enhances sensor rich-to-lean response time; and
   terminating said sputtering of said exhaust electrode onto said given surface before sensor lean voltages and lean-to-rich response times are adversely affected.

2. In a method of sputtering an exhaust electrode onto a given surface of a zirconia solid electrolyte exhaust gas oxygen sensor body, opposite from a surface on said body having a previously formed reference electrode, the improvement of:
   providing a low resistance electrical path between the reference electrode and a sputtering anode;
   sputtering the exhaust electrode onto said given surface at a rate sufficient to heat said sensor body and thereby make it significantly electrically conductive;
   maintaining the exhaust electrode electrically isolated from said reference electrode during said sputtering, so as to maintain a voltage difference between said surfaces during sputtering that electrochemically reduces zirconia to free zirconium adjacent said given surface and oxidizes any free zirconium at said opposite surface, effective to enhance sensor rich-to-lean response time; and
   terminating said sputtering of said exhaust electrode onto said given surface before apparent zirconia reduction progresses from said given surface to said opposite surface, and adversely affects sensor lean voltages and lean-to-rich response times.

3. In a method of sputtering an exhaust electrode onto an outer surface of a hollow thimble zirconia for an exhaust gas oxygen sensor after an inner electrode has been previously formed inside the thimble, the improvement of:
   providing a low resistance electrical path between the inner electrode and a sputtering anode;
   sputtering the exhaust electrode onto said given surface in a nitrogen atmosphere containing 30-50 percent by volume argon at a pressure of about 10-20 millitorr, using a minimum thimble-to-target spacing of about 3.0 cm and a sputtering power of about 13-22 watts/cm$^2$ of target area used, so as to heat the thimble and make it significantly electrically conductive;
   masking a portion of the thimble to maintain the outer surface of the thimble from electrically contacting the inner electrode during sputtering, so as to maintain a voltage difference between the outer surface and the inner electrode during sputtering that enhances sensor rich-to-lean response time; and
   terminating the sputtering before sensor lean voltages and lean-to-rich response times are adversely affected.

4. In a method of sputtering an exhaust electrode onto an outer surface of a hollow zirconia thimble for an exhaust gas oxygen sensor after a reference electrode has been previously formed on its hollow interior, the improvement of:
   providing a low resistance electrical path between the reference electrode and a sputtering anode;
   sputtering the exhaust electrode onto said given surface in an atmosphere consisting essentially of about 50-70 percent by volume of at least one gas selected from the group consisting of oxygen and nitrogen, and the balance an inert gas at a pressure of about 10-20 millitorr using a minimum thimble-to-target spacing of about 3.0 cm and a sputtering power sufficient to heat said sensor body and thereby make it significantly electrically conductive;
   maintaining the exhaust electrode electrically isolated from said reference electrode during said sputtering, so as to maintain a voltage difference between said surfaces during sputtering that electrochemically reduces zirconia to free zirconium adjacent said given surface and oxidizes any free zirconium at said opposite surface, effective to enhance sensor rich-to-lean response time; and
   terminating said sputtering of said exhaust electrode onto said given surface before apparent zirconia reduction progresses from said given surface to said opposite surface, and adversely affects sensor lean voltages and lean-to-rich response times.

* * * * *